United States Patent

Woo

Patent Number: 5,958,876
Date of Patent: Sep. 28, 1999

[54] CYCLOSPORIN-CONTAINING PHARMACEUTICAL COMPOSITIONS

[75] Inventor: Jong Soo Woo, Suwon-shi, Rep. of Korea

[73] Assignee: Novartis AG, Basel, Switzerland

[21] Appl. No.: 09/041,456

[22] Filed: Mar. 12, 1998

Related U.S. Application Data

[63] Continuation-in-part of application No. 08/878,118, Jun. 18, 1997, abandoned, which is a continuation-in-part of application No. PCT/EP97/03213, Jun. 19, 1997.

[51] Int. Cl.$^6$ .............................. A61K 38/00; A61K 9/48
[52] U.S. Cl. .............................. 514/11; 424/451; 530/317
[58] Field of Search .............................. 530/317; 514/11; 424/451

[56] References Cited

U.S. PATENT DOCUMENTS

| | | | |
|---|---|---|---|
| 4,388,307 | 6/1983 | Cavanak | 424/177 |
| 5,342,625 | 8/1994 | Hauer et al. | 424/455 |
| 5,589,455 | 12/1996 | Woo | 514/11 |
| 5,626,872 | 5/1997 | Vasquez | 424/451 |

FOREIGN PATENT DOCUMENTS

| | | |
|---|---|---|
| 539319A2 | 4/1993 | European Pat. Off. . |
| 589843A1 | 3/1994 | European Pat. Off. . |
| 0711550 | 5/1996 | European Pat. Off. . |
| 712631A2 | 5/1996 | European Pat. Off. . |
| 0793966 | 9/1997 | European Pat. Off. . |
| 06247869 | 9/1994 | Japan . |
| 7188046 | 7/1995 | Japan . |
| 2098865 | 12/1982 | United Kingdom . |
| 91/15210 | 10/1991 | WIPO . |
| 96/13273 | 5/1996 | WIPO . |
| 97/22358 | 6/1997 | WIPO . |
| 97/36610 | 10/1997 | WIPO . |

OTHER PUBLICATIONS

Wade et al., Handbook of Pharmaceutical Excipients (1994), pp. 355–361, 648.

Ainley Wade and Paul J. Weller, (eds.), Handbook of Pharmaceutical Excipients, 2nd ed., "Propylene Carbonate," pp. 405–406.

*Primary Examiner*—Cecilia J. Tsang
*Attorney, Agent, or Firm*—William K. Wissing

[57] ABSTRACT

The present invention relates to a cyclosporin-containing soft capsule preparation which contains a composition containing cyclosporin as an active ingredient; a non-hydrophilic component propylene carbonate or a mixture of propylene carbonate and a hydrophilic component polyethylene glycol, one or a mixture of two or more selected from the group consisting of an esterified compound of fatty acid and primary alcohol, medium chain fatty acid triglyceride and fatty acid monoglyceride as an oil component; and a surfactant having an HLB (Hydrophilic Lipophilic Balance) value of 8 to 17.

24 Claims, No Drawings

CYCLOSPORIN-CONTAINING PHARMACEUTICAL COMPOSITIONS

This application is a continuation in part of our copending U.S. applications Ser. No. 08/878,118 filed Jun. 18, 1997, now abandoned as well as PCT Application No. PCT/EP97/03213, filed Jun. 19, 1997 (International Publication No. WO 97/48410).

FIELD OF THE INVENTION

This invention relates to an, e.g. soft capsule, preparation containing cyclosporin as an active ingredient. More specifically, the present invention relates to a soft capsule preparation containing cyclosporin as an active ingredient, propylene carbonate or a mixture of propylene carbonate and polyethylene glycol, an oil component selected from the group consisting of an esterified compound of fatty acid and primary alcohol, medium chain fatty acid triglyceride and fatty acid monoglyceride; and a surfactant having HLB (hydrophilic-lipophilic balance) value of 8 to 17.

BACKGROUND OF THE INVENTION

Cyclosporin is a specific macromolecular (molecular weight 1202.64) cyclic peptide compound consisting of 11 amino acids, which has broad spectrum of useful pharmacological activities, particularly immuno-suppressive activity and anti-inflammatory activity. Therefore, cyclosporin has been used for suppression of inherent immunological responses of the living body, which are caused by tissue and organ transplantation, for example, transplantation of the heart, lung, liver, kidney, pancreas, bone marrow, skin and cornea, and especially the transplantation or foreign tissues and organs. In addition, cyclosporin is useful for the suppression of hematological disorders such as anemia, various autoimmune diseases such as systemic lupus erythematosus, idiopathic malabsorption syndrome, etc., and inflammatory diseases such as arthritis, rheumatoid disorders, etc. Cyclosporin is useful in treatment of protozoal diseases such as malaria, schistosomiasis, etc., and furthermore, recently it is also used in chemotherapy.

Cyclosporin is highly lipophilic and hydrophobic. Therefore, cyclosporin is sparingly soluble in water, and as well dissolved in an organic solvent such as methanol, ethanol, acetone, ether, chloroform and the like. Due to low water-solubility of cyclosporin having above-mentioned properties, when cyclosporin is administered orally, its bioavailability is extremely low and may be greatly influenced by the conditions of each individual patient. Accordingly, it is very difficult to retain an effective therapeutic concentration. Moreover, cyclosporin may show considerable side effects such as nephrotoxicity. Thus, cyclosporin is very difficult to formulate into a preparation for oral administration due to its low water solubility. Accordingly, numerous studies have been extensively conducted to discover a preparation suitable for the effective oral administration of cyclosporin, which can provide a suitable uniform dosage and appropriate bioavailability.

In the prior art, the preparations suitable for oral administration of sparingly water-soluble cyclosporin have been usually formulated in the form of a emulsion pre-concentrate.

One typical method using this combination is taught in U.S. Pat. No. 4,388,307 which issued on Jun. 14, 1983. This patent discloses a liquid formulation of cyclosporin using ethanol. According to the method disclosed in this U.S. Patent Specification, cyclosporin is combined with a carrier consisting of ethanol as a co-surfactant; olive oil as a vegetable oil, and a transesterification product of a natural vegetable oil triglyceride and a polyalkylene polyol as a surfactant to form the liquid formulation. However, the resulting liquid formulation is administered as an aqueous dilution which makes it very difficult to adapt the subject to its administration and to provide a uniform dosage for oral administration.

In order to mitigate the inconvenience of diluting the cyclosporin liquid composition in water prior to oral administration, a liquid composition in the form of an emulsion pre-concentrate has been formulated into a soft capsule preparation, which is now commercially available as Sandimmun®. In this case the cyclosporin soft capsule contains ethanol due to the solubility requirements of cyclosporin. However, since ethanol may permeate the gelatin shell of the capsule as it is volatile even at normal temperature, to prevent the volatilization of ethanol from the soft capsule preparations during storage and distribution, the soft capsule preparations may be wrapped in a special packing material, such as an aluminium-aluminum blister package.

Recently it has been possible to develop a cyclosporin preparation which has a stability during the storage period and further provides substantially no change in biological availability and its difference between individual subjects, so that the biological effect of cyclosporin can be uniformly maintained. One of the preparations developed for this purpose is disclosed in Korean Laid-open Patent Publication No. 93-113. This preparation is commercialized under the registered trademark Sandimmun Neoral. However, since this preparation also uses ethanol, it may have some disadvantages as in the prior ethanol-containing preparations, in storage stability, and changes in the ethanol content.

Accordingly, the present inventors have studied numerous combinations of various surfactants, oil components, co-surfactants etc., to find a cyclosporin composition which is stable, and provides higher bioavailability and lower difference in blood levels between individual subjects than those of the prior cyclosporin preparations in view of their pharmacokinetic properties. As a result, we have identified that a certain cyclosporin composition consisting of the components as defined below can satisfy the above-mentioned requirements, and then completed the present invention.

SUMMARY OF THE INVENTION

Therefore, it is an aspect of the present invention to provide a composition suitable for formulation into soft capsules, which comprises cyclosporin as an active ingredient; a second component selected from the group consisting of propylene carbonate as a non-hydrophilic substance and a mixture of propylene carbonate as a non-hydrophilic substance and polyethylene glycol as a hydrophilic substance; an oil component as defined below, and a surfactant. It is a further aspect of the present invention to provide a soft capsule preparation comprising a composition which contains cyclosporin as an active ingredient; a second component selected from the group consisting of propylene carbonate and a mixture of propylene carbonate and polyethylene glycol; one or a mixture of two or more selected from the group consisting of an esterified compound of fatty acid and primary alcohol, medium chain fatty acid triglyceride (if desired) and fatty acid monoglyceride as an oil component; and a surfactant having an HLB (Hydrophilic Lipophilic Balance) value of 8 to 17. Further it is another aspect of the present invention to provide a process for preparing the soft gelatin capsule preparation as defined above.

Even though the present invention is described herein particularly with respect to soft gelatine capsules, it is to be appreciated that the invention covers the composition itself, which may be used as such e.g. as a drink solution, e.g. as Sandimmun Neoral, or be in other unit dosage forms.

DETAILED DESCRIPTION OF THE INVENTION

In one aspect, the present invention relates to a cyclosporin-containing capsule which has a high storage stability such that there is little variation of the composition over time, and has an increased bioavailability, and which contains a composition comprising cyclosporin as an active ingredient; propylene carbonate as a non-hydrophilic substance or a mixture of propylene carbonate (non-hydrophilic susbstance) and polyethylene glycol (hydrophilic substance) as a second component; an oil component as defined herein below; and a surfactant.

To formulate such cyclosporin-containing composition into the soft capsule preparation, a gelatin shell must be used. However, when the soft capsule is formulated with the general capsule shell containing glycerine as plasticizer, the soft capsule preparation has some disadvantages in that the emulsified state of the emulsion preconcentrate may be changed due to the inflow of glycerine into the emulsion and, therefore, the solubility of cyclosporin is significantly lower to result in the precipitation of cyclosporin from the emulsion. Accordingly, in the present invention preferably a gelatin shell using a mixture of propylene glycol and polyethylene glycol, not glycerine, as a plasticizer is selected for the soft capsule shell, which can solve the problem related with inflow of glycerine.

However, when the capsule shell band containing propylene glycol and polyethylene glycol according to the present invention is prepared by means of a water-cooling method which is conventionally used for a cooling drum, it is not easily removed from the drum. Such removability of the capsule shell band from the cooling drum may be improved by over-cooling the cooling drum by continuously circulating a cooling water to reduce temperature of the band to about 17° C. However, the capsule shell band which is cooled to lower temperature may provide a low extent of seal during the encapsulation process and may cause lowering of productivity.

Therefore, the process for preparing the gelatin shell band not containing glycerine plasticizer according to the present invention adopts an air-cooling method, instead of the prior water-cooling method, in which the capsule shell band can be cooled down to the optimum temperature by providing an air flow from a fan and therefore, can be readily removed from the cooling drum and further, it is maintained at the optimum temperature of about 21° C. to increase the extent of seal in the encapsulation process and ensure a high productivity.

As mentioned above, the present products can be produced by using the glycerine-free gelatin capsule shell and applying the air-cooling method to the composition which does not contain ethanol as a low boiling volatile solvent and therefore, has a high storage stability such that there is little variation of the composition over time, and has an increase bioavailability.

More specifically, the present invention relates to a cyclosporin preparation, which comprises a composition containing 1) cyclosporin as an active ingredient;
2) propylene carbonate or a mixture of propylene carbonate and polyethylene glycol;
3) one or a mixture of two or more selected from the group consisting of an esterified compound of fatty acid and primary alcohol, medium chain fatty acid triglyceride and fatty acid monoglyceride, as an oil component, and
4) a surfactant having an HLB (Hydrophilic Lipophilic Balance) value of 8 to 17, e.g. in a gelatin shell containing polyethylene glycol and propylene glycol as a plasticizer. In another aspect, the present invention provides a cyclosporin preparation, which comprises a composition containing 1) cyclosporin as an active ingredient; and
2) propylene carbonate. In certain embodiments of the invention, the cyclosporin preparations are free of polyethylene glycol as a second component.

Such compositions, which are also a composition or the invention, may optionally additionally comprise any other component as described herein, if desired in the amounts described herein.

Cyclosporin, a cyclic peptide compound having useful immuno-suppressive activity and anti-inflammatory activity as described above, is the first essential component of the compositions of the present invention and is used as the pharmaceutically active ingredient therein. Although cyclosporin A, B, C, D, G and the like can be used as the cyclosporin component in the present invention. Cyclosporin A is mostly preferred since its clinical effectiveness and pharmacological properties are well established in the art.

As the essential component in the composition according to the present invention, and which may act as a co-surfactant, propylene carbonate, which has a high boiling point (about 242° C.), is non-volatile, shows low hygroscopic property and shell permeability, and has a high solubility for cyclosporin, is used as the non-hydrophilic substance.

Optionally, polyethylene glycol, which has a high boiling point, is non-volatile, does not permeate the gelatin shell of the soft capsule, and has a high solubility for cyclosporin, can also be used as the hydrophilic substance, in mixture with the propylene carbonate. In the composition according to the present invention, although any polyethylene glycol which can be liquified can be used, polyethylene glycol (PEG) having molecular weight of 200 to 600, particularly PEG 200, can be preferably used. When the mixture of polyethylene glycol and propylene carbonate is used as the second component in the present invention, they can be generally combined in the ratio of 1:0.1–5, preferably 1:0.1–3, most preferably 1:0.2–2, on the basis of weight.

In the present invention, the use of the mixture of polyethylene glycol and propylene carbonate provides certain advantages. That is, the stability of the cyclosporin-containing composition during storage is improved and therefore the contents of the components contained therein are substantially uniformly maintained. Furthermore, the use of propylene carbonate can even increase the solubility of the active ingredient cyclosporin and inhibit the inflow of water from the gelatin capsule shell into the composition to provide a more stable composition.

In the composition of the present invention, the second component is used preferably in the ratio of 0.1 to 10 parts by weight, more preferably 0.5 to 8 parts by weight, and most preferably 1 to 5 parts by weight, per 1 part by weight of cyclosporin.

The essential component used in the emulsion pre-concentrate according to the present invention is an oil component. As the oil component in the present invention, one or a mixture of two or more selected from the group consisting of esterified compounds of fatty acid and primary alcohol (fatty acid ester), medium chain fatty acid triglycerides (when present) and fatty acid monoglycerides can be used. The esterified compound of fatty acid and primary alcohol which can be used in the present invention may include an esterified compound of fatty acid having 8 to 20 carbon atoms and primary alcohol having 2 to 3 carbon atoms, for example, isopropyl myristate, isopropyl palmitate, ethyl linoleate, ethyl oleate, etc., with an esterified compound of linoleic acid and ethanol being particularly preferable. In addition, as the medium chain fatty acid triglyceride (when present) a triglyceride of saturated fatty acid having 8 to 10 carbon atoms can be used with caprylic/capric acid triglyceride as a vegetable oil triglyceride of saturated fatty acid being most preferably used. The fatty acid monoglyceride which can also be used as the oil component in the present invention includes a monoglyceride of fatty acid having 18 to 20 carbon atoms, particularly monoglyceride of oleic acid.

In a microemulsion pre-concentrate according to the present invention, the oil component may be used in the ratio of 1 to 10 parts by weight, preferably 2 to 6 parts by weight, per 1 part by weight of cyclosporin.

In certain embodiments, the oil component comprises a mixture of the esterified compound of fatty acid and primary alcohol, medium chain fatty acid triglyceride and fatty acid monoglyceride. Preferably, mixtures of fatty acid monoglyceride and fatty acid ester are present as oil component, e.g. in the ratio 1:1–2, e.g. 1:1–1.2. Optionally caprylic/capric acid triglyceride is also present e.g. in a ratio to ethyl linoleate of from 1:0.1–0.2.

In the oil mixture used as the oil component according to the present invention, the mixing ratio of fatty acid monoglyceride: an esterified compound of fatty acid and primary alcohol:medium chain fatty acid triglyceride (when present) may be generally in the range of 1:0.1–5;0.1–10 preferably in the range of 1:0.1–3.0:0.1–3.0, on the basis of weight.

The essential component used in the composition according to the present invention is a surfactant. The suitable surfactants for use in the present invention include any of pharmaceutically acceptable surfactants having an HLB (Hydrophilic Lipophilic Balance) value of 8 to 17, which are capable of stably emulsifying the lipophilic portion of the composition comprising the cyclosporin-containing oil component and the hydrophilic portion comprising the second component co-surfactant in water to form a stable microemulsion. Examples of the preferred surfactant according to the present invention include polyoxyethylene products of hydrogenated vegetable oils, polyoxyethylene-sorbitan-fatty acid esters, and the like, for example, NIKKOL HCO-50, NIKKOL HCO_40, NIKKOL HCO-60, TWEEN 20, TWEEN 21, TWEEN 40, TWEEN 60, TWEEN 80, TWEEN 81, etc. Particularly, a polyoxyethylene (50) hydrogenated castor oil which is commercialised under the trade mark NIKKOL HCO-50 (NIKKO Chemical Co., Ltd.) and a polyoxyethlyene (20) sorbitan monolaurate which is commercialised under the trade mark TWEEN 20 (ICI Chemicals), having an acid value below 1, a saponification value of about 48–56, a hydroxyl value of about 45–55 and pH value (5%) of 4.5–7.0, can be preferably used.

The surfactant can include any one of the above-mentioned surfactants alone or, preferably, in a combination of two or more surfactants selected from the above surfactants. In the composition according to the present invention, the surfactants can be used in the ratio of 1 to 10 parts by weight, preferably in the ratio of 2 to 8 parts by weight, per 1 part by weight of cyclosporin.

In addition, when the mixture of two surfactants, i.e. polyoxyethylene (50) hydrogenated castor oil and polyoxyethylene (20) sorbitan monolaurate is used in the composition of the present invention, the constitutional ratio of polyoxyethylene (50) hydrogenated castor oil:polyoxyethylene (20) sorbitan monolaurate is preferably in the range of 1:0.1–5, more preferably in the range of 1:0.5–4, on the basis of weight.

In the composition according to the present invention, the four components are present preferably in the ratio of cyclosporin:second component; oil component;surfactant= 1:0.1–10:1–10:1–10, and more preferably in the ratio of cyclosporin: second component:oil component:surfactant= 1:0.5–8:2–6:2–8, by weight. In addition to this composition, the composition illustrated in the following examples can be mentioned as further preferred compositions according to the present invention.

For oral administration, the composition of the present invention containing the above-mentioned components can be formulated into the form of a soft capsule. Since the soft capsule preparation according to the present invention does not use ethanol as the low-boiling volatile solvent, it is pharmaceutically stable and can establish the desired improvements including improvement of bioavailability. However, it may be difficult to reproductively prepare as a conventional soft capsule shell by means of a conventional method for preparation of soft capsules. When the soft capsule is formulated with the conventional capsule shell containing glycerine as plasticizer, the soft capsule thus prepared may have some disadvantages in that the emulsified state of the emulsion pre-concentrate may be changed due to the inflow of glycerine into the emulsion and therefore, the solubility of cyclosporin is significantly lowered which may result in the precipitation of cyclosporin from the emulsion.

Accordingly, in another aspect of the present invention it is found that when the capsule shell is formulated by using a mixture of polyethylene glycol and propylene glycol, not glycerine, as a plasticizer, the soft capsule preparation which is stable for a long period can be obtained. Although any polyethylene glycol which can be liquified may be used as a plasticizer, it is preferable to use polyethylene glycol having molecular weight of 200 to 600. Particularly, polyethylene glycol 200 is preferably used. In the soft capsule shell according to the present invention, the mixture of polyethylene glycol and propylene glycol is preferably used in the ratio of 0.1 to 0.5 parts by weight, more preferably 0.1 to 0.4 parts by weight and most preferably 0.2 to 0.3 parts by weight, with respect to one part by weight of gelatin used for preparing the capsule shell. In the mixture of polyethylene glycol and propylene glycol as the plasticizer, propylene glycol is combined preferably in the ratio or 1 to 10 parts by weight, more preferably 3 to 8 parts by weight and most preferably 3 to 6 parts by weight, with respect to one part by weight of polyethylene glycol.

In order to increase the removability of the soft capsule shell band from the cooling drum, the process for preparing the gelatin capsule shell band according to the present invention adopts the air-cooling method, instead of the water-cooling method. According to this air-cooling method, since the capsule shell band is not overheated and can be readily removed from the cooling drum while maintaining the optimum temperature of about 21° C., the extent of seal in the encapsulation process is high to ensure a high productivity and therefore, the process can be efficiently conducted.

In preparing the soft capsule according to the present invention, a suitable air volume flow for the cooling drum to cool the capsule shell is preferably 5 to 15 m³/min., most preferably about 10 m³/min.

Since as the second component in the present invention propylene carbonate may be used alone or as a main component thereof, cyclosporin-containing soft capsule preparations which are stable for long time can be formulated without using a certain plasticizer in a gelatin shell, considering a solubility of cyclosporin and a stability of soft capsule.

In such a gelatin shell, the plasticizer, one or more selected from the group consisting of glycerine, sorbitol, hexanetriol, propylene carbonate, hexane glycol, sorbitans, tetrahydrofuryl alcohol ether, diethylene glycol monoethyl ether, 1,3-dimethyl-2-imidazolidone, dimethylisosorbide, etc. can be used without any limitation. However, it should be understood that the plasticizer which can be used in the present invention is not restricted to those as mentioned above.

In formulating the composition according to the present invention into soft capsules, the capsule preparation can further contain, if necessary, pharmaceutically acceptable additives which are conventionally utilized in the preparation of soft capsules. Such additives include, for example, lecithin, viscosity regulator, perfume (e.g. peppermint oil, etc.), anti-oxidant (e.g. tocopherol, Vitamin E etc.), preservative (e.g. parabene, etc.), coloring agent, amino acids, etc.

The soft capsule preparation according to the present invention can be prepared by uniformly mixing the second component, the oil component and the surfactant, dissolving cyclosporin therein while stirring and gently warming to the temperature of approximately 60° C., and then formulating the resulting concentrate, with or without the above-mentioned pharmaceutically acceptable additives conventionally utilized in preparation of soft capsules, with the gelatin shell containing polyethylene glycol and propylene glycol as the plasticizer in a machine for preparing soft capsules by means of the air-cooled method into the desired suitable cyclosporin soft capsule.

The compositions and preparations of the present invention are useful for the same indications and may be administered in the same way and dosage range as known cyclosporin compositions, if necessary adjusting the dose on the basis of standard bioavailability trials in animals, e.g. dogs, or humans, e.g. as described hereinafter.

Insofar as details of the compositions of any excipients or components are not specifically described herein, these are described in the literature, e.g. H. P. Fiedler, Lexikon der Hilfsstoffe, Edito Cantor Verlag, Aulendorf, Germany, 4th Edition 1996, Handbook of Pharmaceutical Excipients, American Pharmaceutical Association, Washington, and The Pharmaceutical Society, London, 2nd Edition, 1994 and Korean Patent Application 94-29208 filed Sept. 11, 1994.

The present invention will be more specifically illustrated by the following examples. However, it should be understood that the present invention is not limited by these examples in any manner.

| EXAMPLES: Component | 1 | 2 | 3 | 4 | 5 |
|---|---|---|---|---|---|
| | | | Content (mg/Cap.) | | |
| Cyclosporin | 25 | 25 | 25 | 25 | 25 |
| polyethylene glycol 200 | 45 | 70 | 100 | 45 | 45 |
| propylene carbonate | 25 | — | 50 | 25 | 25 |
| polyoxyethylene (50) hydrogenated castor oil | 35 | 35 | 35 | 50 | 35 |
| polyoxyethylene (20) sorbitan monolaurate | 85 | 85 | 85 | 100 | 85 |
| ethyl linoleate | 40 | 40 | 40 | 40 | 80 |
| caprylic/capric acid triglyceride | 5 | 5 | 5 | 5 | 10 |
| oleic acid monoglyceride | 35 | 35 | 35 | 35 | 70 |
| total | 295 mg | 295 mg | 375 mg | 325 mg | 375 mg |

EXAMPLE 6

The soft capsule preparation was prepared from the composition of Example 1 using the following composition for capsule shell and then the change in the property and condition of the content due to the inflow of glycerine was visually observed.

| | Component | Weight ratio |
|---|---|---|
| 6.1 | (control group) | |
| | gelatin | 20 |
| | purified water | 16 |
| | glycerine | 9 |
| 6.2 | (test group) | |
| | gelatin | 20 |
| | purified water | 16 |
| | propylene glycol | 4 |
| | polyethylene glycol 200 | 1 |

TABLE 1

Stability of the content of the capsule preparation according to the capsule shell.

| Composition of Capsule | Just after formulation | After 1 day | After 2 days | After 5 days | After 10 days | After 30 days |
|---|---|---|---|---|---|---|
| Control group | 0 | + | + | ++ | +++ | +++ |
| Test group | 0 | 0 | 0 | 0 | 0 | 0 |

Note: 0 = the content is stable
+ = poor emulsification
++ = slight precipitation
+++ = precipitation As can be seen from the result described in table 1, the capsule preparation prepared using the composition of 6.1 control group containing glycerine as the plasticizer causes some problems including the formation of precipitation due to the inflow of glycerine, whereas the capsule preparation prepared using the composition of 6.2 test group containing polyethylene glycol and propylene glycol as the plasticizer maintains the stable condition.

EXAMPLE 7

The soft capsule preparation having the composition of Example 1 was prepared using the composition of the capsule shell of 7.2 test group used in the above Example 6 by means of the water-cooling method (water temperature about 12° C.) and the air-cooling method (air volume flow about 10 m³/min), respectively. In each case, the removability of the capsule shell band from the cooling drum was observed and compared. The result as observed is described in the following Table 2.

TABLE 2

Removability of the gelatin shell band from the cooling drum depending on the cooling method

| Shell Composition | Water-cooling Method | (Unit: degree of angle) Air-cooling Method |
|---|---|---|
| Example 6.2 | >100 degree (poor removability) | <50 degree (good removability) |

As can be seen from the result described in the Table 2 above, the soft capsule preparation prepared by the air-cooling method according to the present invention shows a far better removability from the cooling drum in comparison with that prepared by the water-cooling method. Specifically, it is generally considered that if the degree of angle for removing the gelatin shell band from the cooling drum is about 70 or more, the removability is poor, and if the degree of angle for removing the shell band is below about 70, the removability is good. The soft capsule preparation prepared by the water-cooling method is not satisfactorily removed from the cooling drum even when the preparation is removed at the angle of 100 degrees or more. Contrary to this, the soft capsule preparation prepared by the air-cooling method according to the present invention can be easily removed from the cooling drum at the angle of 50 degree and below and therefore, can provide a good sealing strength and productivity.

EXAMPLE 9

The bioavailability of the preparation prepared by encapsulating the composition of Example 1 with the gelatin shell having the composition of Example 6.2 as the test preparation was compared with the bioavailability of the commercial product containing ethanol, SANDIMMUN Capsule, as the control preparation to estimate the influence of the cyclosporin preparation according to the present invention on the bioavailability of cyclosporin and its difference between respective subjects.

In this experiment, both of the test preparation and the control preparation were administered in an amount of 300 mg as cyclosporin per kg of rabbit. Rabbits were uniformly fed with the conventional rabbit solid feed composition for 4 days or more under the same condition in wire cages. When the oral preparation were administered, rabbits were fasted for 48 hours in a restraint cage made of steel, during which rabbits were allowed to freely take water.

Levin's tube having a diameter of 5 mm was interposed by the depth of 30 cm through the esophagus after the surface of the Levin's tube was coated with vaseline in order to reduce friction. Each of the test preparations and the control preparation was emulsified with 50 ml of water and then introduced into a syringe which is attached to the Levin's tube. Ear veins of rabbit were dilated using xylene and then blood was taken from each rabbit's ear vein before the test and after 0.5, 1, 1.5, 2, 3, 4, 6, 10 and 24 hours by means of heparin-treated disposable syringe. To 1 ml of blood thus obtained were added 0.5 ml of aqueous saturated sodium chloride solution and 2 ml of ether, and then the mixture was shaken for 5 minutes and centrifuged with 5000 rpm for 10 minutes to separate the supernatant (ether layer). 1 ml of the supernatant was collected and then developed in an activated silica sep-pak® (Waters). The developed sep-pak was washed with 5 ml of n-hexane and eluted with 2 ml of methanol. The eluate was evaporated to dryness in nitrogen gas under reduced pressure. The residue was analysed by means or HPLC (High Performance Liquid Chromatography) [HPLC condition: column $\mu$-Bondapak® $C_{18}$ (Waters), mobile phase $CH_3CN$: MeOH; $H_2O$ - 55:15:30, detection 210 nm, flow rate 1.0 ml/min., column temperature 70° C., sensitivity 0.01 Aufs. injection volume 100 $\mu$l].

The results obtained from the test preparation and the control preparation are illustrated in the following Table 3:

TABLE 3

Bioavailability of the test preparation of the present invention and the commercial product (SANDIMMUN)

| Parameter (B/A) | Control Prep. (A) | | Test Prep. (B) | |
|---|---|---|---|---|
| | M ± S.D. (n = 6) | CV % (S.D./M) | M ± S.D. (n = 6) | CV % (S.D./M) |
| AUC | 13.5 ± 10.0 4.1 ($\mu$g.hr/ml) | 74.0% | 57.0 ± 17.0 | 29.8% |
| $C_{max}$ | 0.8 ± 0.3 7.5 ($\mu$g.hr/ml) | 37.5% | 6.0 ± 1.5 | 25.0% |

Note: AUC = Area under the blood concentration curve
$C_{max}$ = Maximum blood concentration of cyclosporin
M ± S.D. = Mean value ± Standard deviation
CV = Ratio of standard deviation to mean value
P(B/A) = Ratio of mean value of the test preparation to mean value of the control preparation As can be seen from the above table, the test preparation shows the increased AUC and $C_{max}$ values which are about 4 times or more and about 7 times or more, respectively, as high as those of the control preparation. Accordingly, it can be identified that the bioavailability of the test preparation is significantly increased in comparison with that of the control preparation. In addition, the test preparation of the present invention exhibits an effect of decreasing the difference between respective test subjects (CV %) by about 2 times or more in AUC value and by about 1.5 times in $C_{max}$ value, in comparison with the control preparation.

Accordingly, it could be determined that when the soft capsule preparation according to the present invention is administered per oral, it shows the increased bioavailability of cyclosporin about 4 times as high as that of the prior commercial product containing ethanol, SANDIMMUN Capsule and also a decrease of the difference between cyclosporin bioavailabilities in respective subjects, and at the same time, remains stable without any change during the long term storage. Thus, it is apparent that the soft capsule preparation according to the present invention provides a significant improvement in the field of preparation of cyclosporin soft capsules.

EXAMPLE 9

Soft gels are made up containing:

| | I | | II | |
|---|---|---|---|---|
| Cyclosporin A | 25 | mg | 100 | mg |
| Polyethylene glycol 200 | 45 | mg | 180 | mg |
| Propylene carbonate | 25 | mg | 100 | mg |
| Polyoxyethylene 50-hydrogenated castor oil | 40 | mg | 160 | mg |
| Polysorbate 20 | 85 | mg | 340 | mg |
| Ethyl linoleate | 40 | mg | 160 | mg |
| Glyceryl mono-oleate | 40 | mg | 160 | mg |
| Vitamin E | 1 | mg | 4 | mg |
| Total | 301 | mg | 1204 | mg |

EXAMPLES 10 11 12 13 14

| Component | Content (mg/Cap.) | | | | |
|---|---|---|---|---|---|
| Cyclosporin | 25 | 25 | 100 | 25 | 25 |
| propylene carbonate | 50 | 100 | 200 | 50 | 100 |
| polyoxyethylene (50) hydrogenated castor oil | 90 | 80 | 300 | 90 | 90 |
| polyoxyethylene (20) sorbitan monolaurate | 80 | 80 | 280 | 80 | 80 |
| ethyl linoleate | 40 | 30 | 150 | — | 40 |
| caprylic/capric acid triglyceride | 5 | 10 | 20 | 5 | 5 |
| oleic acid monoglyceride | 35 | 50 | 120 | 35 | 35 |
| Labrafil | — | — | 50 | — | — |
| total | 325 mg | 375 mg | 1220 mg | 285 mg | 375 mg |

EXAMPLES 15 16 17 18

| Component | Content (mg/Cap.) | | | |
|---|---|---|---|---|
| Cyclosporin | 25 | 25 | 25 | 25 |
| polyethylene glycol 200 | 35 | 50 | 25 | 20 |
| propylene carbonate | 45 | 100 | 45 | 80 |
| polyoxyethylene (50) hydrogenated castor oil | 30 | 35 | 50 | 35 |
| polyoxyethylene (20) sorbitan monolaurate | 80 | 90 | 75 | 85 |
| ethyl linoleate | 35 | 40 | 40 | 80 |
| caprylic/capric acid triglyceride | 5 | 5 | 5 | 10 |
| oleic acid monoglyceride | 35 | 30 | 35 | 85 |
| total | 290 mg | 375 mg | 300 mg | 420 mg |

EXAMPLE 19

The bioavailability of the soft capsule preparation prepared from the composition of Example 10 according to a conventional manner as the test preparation was compared with the bioavailability of the commercial product containing ethanol, SANDIMMUN Capsule, as the control preparation to estimate the influence of the cyclosporin preparation according to the present invention on the bioavailability of cyclosporin and its difference between respective subjects.

The experimental protocol was the same as under Example 8 described.

The results obtained from the test preparation and the control preparation are illustrated in the following Table 4:

TABLE 4

Bioavailability of the test preparation of the present invention and the commercial product (SANDIMMUN)

| | Control Prep. (A) | | Test Prep. (B) | |
|---|---|---|---|---|
| Parameter (B/A) | M ± S.D. (n = 6) | CV % (S.D./M) | M ± S.D. (n = 6) | CV % (S.D./M) |
| AUC | 13.5 ± 10.0 4.4 (μg.hr/ml) | 74.0% | 60.1 ± 18.0 | 30.8% |
| $C_{max}$ | 0.8 ± 0.3 7.7 (μg.hr/ml) | 37.5% | 6.2 ± 1.5 | 24.2% |

Note: AUC = Area under the blood concentration curve
$C_{max}$ = Maximum blood concentration of cyclosporin
M ± S.D. ± Mean value ± Standard deviation
CV = Ratio of standard deviation to mean value
P(B/A) = Ratio of mean value of the test preparation to mean value of the control preparation As can be seen from the above table, the test preparation shows the increased AUC and $C_{max}$ values which are about 4 times or more and about 7 times or more, respectively, as high as those of the control preparation. Accordingly, it can be identified that the bioavailability of the test preparation is significantly increased in comparison with that of the control preparation. In addition, the test preparation of the present invention exhibits an effect of decreasing the difference between respective test subjects (CV %) by about 2 times or more in AUC value and by about 1.5 times in $C_{max}$ value, in comparison with the control preparation.

Accordingly, it could be determined that when the soft capsule preparation according to the present invention is administered per oral, it shows the increased bioavailability of cyclosporin about 4 times as high as that of the prior commercial product containing ethanol, SANDIMMUN Capsule and also a decrease of the difference between cyclosporin bioavailabilities in respective subjects, and at the same time, remains stable without any change during the long term storage. Thus, it is apparent that the soft capsule preparation according to the present invention provides a significant improvement in the field of preparation of cyclosporin soft capsules.

What is claimed is:

1. A pharmaceutical composition, comprising:
   (1) pharmacologically effective amounts of cyclosporin,
   (2) propylene carbonate,
   (3) an oil component selected from the group consisting of an esterified compound of fatty acid and primary alcohol, medium chain fatty acid triglyceride and fatty acid monoglyceride; and
   (4) a surfactant having HLB (Hydrophilic-lipophilic balance) value of 8 to 17,
   wherein said cyclosporin, said propylene carbonate, said oil component and said surfactant are present in a ratio of 1:0.1–10:1–10:1–10, respectively, on the basis of weight.

2. The pharmaceutical composition of claim 1, wherein said medium chain fatty acid triglyceride comprises a triglyceride having fatty acids of 8 to 10 carbon atoms.

3. The pharmaceutical composition of claim 2, wherein said medium chain fatty acid triglyceride is caprylic/capric acid triglyceride.

4. The pharmaceutical composition of claim 1 wherein said fatty acid monoglyceride is a monoglyceride of oleic acid.

5. The pharmaceutical composition of claim 1 wherein said esterified compound of fatty acid and primary alcohol comprises a fatty acid having 8 to 20 carbon atoms and a primary alcohol having 2 to 3 carbon atoms.

6. The pharmaceutical composition of claim 5 wherein said esterified compound of fatty acid and primary alcohol is ethyl linoleate.

7. The pharmaceutical composition of claim 1 wherein said surfactant is selected from the group consisting of a polyoxyethylene product of hydrogenated vegetable oil and a polyoxethylene-sorbitan-fatty acid ester.

8. The pharmaceutical composition of claim 7 wherein said surfactant comprises a mixture of a polyoxyethylene (50) hydrogenated castor oil and a polyoxyethlyene(20) sorbitan monolaurate in a mixing ratio of 1:0.1–5 on the basis of weight.

9. The pharmaceutical composition of claim 1 wherein said cyclosporin, said propylene carbonate, said oil component and said surfactant are present in the ratio of 1:0.5–8:2–6:2–8 on the basis of weight.

10. The pharmaceutical composition of claim 1 further comprising polyethylene glycol having a molecular weight of 200 to 600, said polyethylene glycol and said propylene carbonate being present in a ratio of 1:0.1–5 on the basis of weight.

11. The pharmaceutical composition of claim 1 which is free from polyethylene glycol.

12. The pharmaceutical composition of claim 1 wherein said oil component is a mixture of said esterified compound of fatty acid and primary alcohol, said medium chain fatty acid triglyceride and said fatty acid monoglyceride.

13. The pharmaceutical composition of claim 12 wherein the ratio of said esterified compound of fatty acid and primary alcohol:said medium chain fatty acid triglyceride: :said fatty acid monoglyceride is 1:0.1–5:0.1–10 on the basis of weight.

14. The pharmaceutical composition of claim 1 wherein said oil component is a mixture of said esterified compound of fatty acid and primary alcohol and said fatty acid monoglyceride.

15. The pharmaceutical composition of claim 14 wherein the ratio of said esterified compound of fatty acid and primary alcohol:said fatty acid monoglyceride is 1:1–2 on the basis of weight.

16. The pharmaceutical composition of claim 1 wherein said oil component is a mixture of said medium chain fatty acid triglyceride and said fatty acid monoglyceride.

17. The pharmaceutical composition of claim 1 wherein said pharmaceutical composition is encapsulated in a gelatin capsule which comprises a mixture of propylene glycol and polyethylene glycol as plasticizer, said mixture of propylene glycol and polyethylene glycol being present in a ratio of 0.1 to 5 part by weight with respect to one part by weight of the gelatin.

18. The pharmaceutical composition of claim 17 wherein said plasticizer propylene glycol is combined in the ratio of 1–10 part by weight with respect to one part by weight of polyethylene glycol.

19. A pharmaceutical composition, comprising:
   (1) pharmacologically effective amounts of cyclosporin,
   (2) propylene carbonate,
   (3) an oil component comprising a mixture of a medium chain fatty acid triglyceride and a fatty acid monoglyceride; and
   (4) a surfactant having HLB (Hydrophilic-lipophilic balance) value of 8 to 17,
   wherein said cyclosporin, said propylene carbonate, said oil component and said surfactant are present in a ratio of 1:0.1–10:1–10:1–10, respectively, on the basis of weight.

20. The pharmaceutical composition of claim 19 wherein said fatty acid monoglyceride is a monoglyceride of oleic acid.

21. The pharmaceutical composition of claim 19 wherein said medium chain fatty acid triglyceride comprises a triglyceride having fatty acids of 8 to 10 carbon atoms.

22. The pharmaceutical composition of claim 19 wherein said surfactant comprises a polyoxyethylene product of hydrogenated vegetable oil.

23. The pharmaceutical composition of claim 22 wherein said surfactant comprises a polyoxyethylene hydrogenated castor oil.

24. The pharmaceutical composition of claim 19 which is free from polyethylene glycol.

* * * * *